(12) United States Patent
Saunders et al.

(10) Patent No.: US 7,175,667 B2
(45) Date of Patent: Feb. 13, 2007

(54) METATARSOPHALANGEAL RESURFACING JOINT

(76) Inventors: Gerald Anthony Briden Saunders, 1018 Cliffside Lane, R.r.#1, Sydenham, Ontario (CA) K0H 2T0; Charles Sorbie, 208 Alwington Place, Kingston, Ontario (CA) K7L 4P8

(*) Notice: Subject to any disclaimer, the term of this patent is extended or adjusted under 35 U.S.C. 154(b) by 440 days.

(21) Appl. No.: 10/769,957

(22) Filed: Feb. 2, 2004

(65) Prior Publication Data

US 2004/0230313 A1   Nov. 18, 2004

Related U.S. Application Data

(63) Continuation-in-part of application No. 09/997,343, filed on Nov. 29, 2001, now abandoned.

(51) Int. Cl.
*A61F 2/42* (2006.01)
(52) U.S. Cl. ................................... 623/21.19
(58) Field of Classification Search .. 623/21.11–21.19, 623/19.12, 19.13
See application file for complete search history.

(56) References Cited

U.S. PATENT DOCUMENTS

| 5,314,486 | A | * | 5/1994 | Zang et al. | ............... | 623/21.19 |
| 5,326,366 | A | * | 7/1994 | Pascarella et al. | ....... | 623/21.19 |
| 5,702,469 | A | * | 12/1997 | Whipple et al. | ......... | 623/21.15 |
| 5,725,585 | A | * | 3/1998 | Zobel | ...................... | 623/21.19 |
| 5,782,927 | A | | 7/1998 | Klawitter et al. | | |

* cited by examiner

*Primary Examiner*—Bruce Snow
(74) *Attorney, Agent, or Firm*—Shughart Thomson & Kilroy PC; Richard P. Stitt

(57) ABSTRACT

The present invention provides a prosthesis for implantation at the proximal articular surface of a proximal phalange, of a human great toe. The prosthesis comprises a base portion having a generally concave bearing surface shaped to articulate with the distal articular surface of a metatarsal bone, and a flat surface opposite the bearing surface for emplacement against a resected surface of the proximal phalange of the great toe of the human subject. A stem extends distally from the flat surface of the base portion, for implantation in the intramedulary canal of a proximal phalange of the great toe of the human subject. The stem has a generally frustoconical shape, with a substantially oval wide end at the flat surface of the base portion, tapering to a substantially circular end. The generally frustoconically shaped stem has a longitudinal axis that is inclined at an anatomical angle, of about 94° to the base portion, to align with the intramedulary canal of a proximal phalanx of the great toe of the human subject.

10 Claims, 3 Drawing Sheets

SECTION A-A

SECTION B-B

METATARSOPHALANGEAL RESURFACING JOINT

This is a Continuation-in-Part application of U.S. application Ser. No. 09/997,343 filed Nov. 29, 2001 now abandoned.

FIELD OF THE INVENTION

The invention relates to an implant that resurfaces a bone, in particular the proximal phalanx of the great toe in the metatarsophalangeal.

BACKGROUND OF THE INVENTION

Great toe implant devices have been used to replace the defective natural metatarsophalangeal (MTP) joints. Hemi-joint replacement is generally preferred to full joint replacement when the proximal phalanx in the great toe still has good bone stock and the first metatarsal has an integral head. The implants are used to remove pain in the first metatarsal joint incurred from inflammatory arthritis and to restore joint kinetics by replacing the damaged base portion of the proximal phalanx.

U.S. Pat. No. 5,326,366 to Pascerella et. al. discloses an implant device which has an elliptical base with a concave bearing surface that has an anafomically shaped proximal articular surface with an enlarged build-up on the lateral end thereof, and an elongated stem extends distally from the seating surface of the base which includes an array of fins together having a cruciate-shaped cross-section.

U.S. Pat. No. 5,725,585 to Zobel shows a phalangeal component that has an anatomically correct concave bearing surface, a stem that is a trapezoid in cross-section, and spikes on the rear surface of the implant engaging in the proximal phalanx, preventing rotation of the implant.

A proximal phalanx implant in any of the above prior art has a stem projecting perpendicular from the centre of the base. This is anatomically incorrect when the implant is inserted into the bone. The proximal base of the proximal phalanx has an angular relation to the shaft of the proximal phalanx. As the result, the maximum stability of the implant can not be achieved.

The present invention describes an improved implant with a generally ovoid bone plate having a concave bearing surface reciprocal to the shape of a head of a metatarsal bone. The implant includes a stem that has a generally anatomical relationship to the intramedulary canal of a proximal phalanx. In a preferred embodiment, the stem of the implant of the present invention is surface treated and/or, grooved, making it possible to surgically implant the device without bone cement, and with less surface preparation.

It will be understood that there is a need for the development of an improved great toe implant that provides maximum stability and optimal fixation to the bone for a long period of time, which is relatively straightforward for a surgeon to implant, with or without bone cement.

SUMMARY OF THE INVENTION

It is an object of the present invention to provide an anatomically correct metatarsophalangeal implant that is an improvement of over the prior art.

In a broad aspect, the present invention provides a prosthesis for implantation at the proximal articular surface of a proximal phalange, of a human great toe. The prosthesis comprises a base portion having a generally concave bearing surface shaped to articulate with the distal articular surface of a metatarsal bone, and a flat surface opposite the bearing surface for emplacement against a resected surface of the proximal phalange of the great toe of the human subject. A stem extends distally from the flat surface of the base portion, for implantation in the intramedulary canal of a proximal phalange of the great toe of the human subject. The stem has a generally frustoconical shape, with a substantially oval wide end at the flat surface of the base portion, tapering to a substantially circular end. The generally frustoconically shaped stem has a longitudinal axis that is inclined at an anatomical angle, of about 94° to the base portion, to align with the intramedulary canal of a proximal phalanx of the great toe of the human subject.

In a preferred form, the stem has a side surface that tapers inwardly.

Moreover, it is also preferred that the side surface of the stem is somewhat flattened in three aspects, between the base and end of the stem.

The surface of the stem may be textured for adhesion to the inner surface of an intramedulary canal.

Alternatively, the surface of the stem is ridged in a series of ridges that extend around the stem, parallel to the base portion.

The ridges may be substantially barb-like. Each of the barb-like ridge includes a long flat portion almost parallel to the side surface of the stem, and a short inwardly directed portion at a greater angle to the side surface of the stem.

In another preferred form, the side surfaces of the stem, where flattened, are knurled by cross-hatching. In corner areas between the flattened aspects, barb-ike ridges are provided.

Each of these barb-like ridges comprise an arcuate portion having a surface almost parallel to the side surface of the stem, and a short inwardly directed portion at a greater angle to the side surface of the stem.

The present metatarsophalangeal implant enjoys a number of advantages and improvements over the prior art. For instance, the stability of the implant has been increased by anatomically shaping the stem to the intramedulary canal of the proximal phalanx. An anatomically shaped stem conforms to the endosteal cortex in the shaft, and hence maximizes the stability and optimizes the fixation of the implant to the bone. The bearing surface of the implant is angulated to align with the articulating surface of the proximal phalanx to maintain proper biomechanics with the joint. The base plate is positioned at an anatomical angle with the stem following the anatomic angular relation between the shaft and the proximal base of the proximal phalanx, which further increases the stability of the implant secured in the bone. The stem is surface treated to further improve the adhesion of the stem to the intramedulary canal of a bone.

In a preferred embodiment, the surface of the stem of the implant of the present invention may be knurled by cross-hatching or checking, to provide an effective gripping surface. The surface may be provided with a combination of checked and grooved areas, to further enhance grip in the intramedulary canal.

Other advantages, objects and features of the present invention will be readily apparent to those skilled in the art from a review of the following detailed description of the preferred embodiments in conjunction with the accompanying drawings and claims.

BRIEF DESCRIPTION OF THE DRAWINGS

Preferred embodiments of the present invention will now be described in greater detail and will be better understood when read in conjunction with the following drawings, in which.

DETAILED DESCRIPTION OF THE PREFERRED EMBODIMENTS

Figure 1:
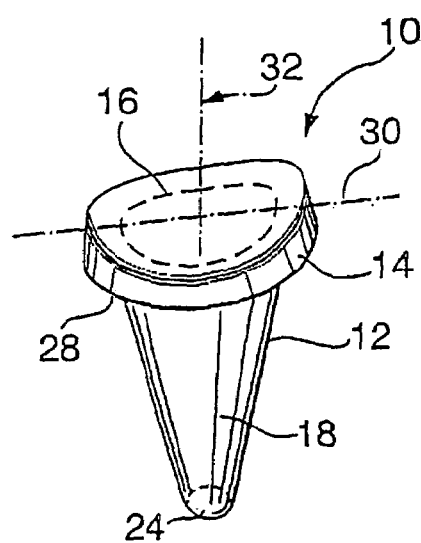
FIG. 1 is a perspective view of an implant in accordance with the present invention.

Referring to FIG. 1, a great toe implant 10 has a base plate 14 coupled to an elongated stem 18, which is adapted to be inserted in the intramedulary canal of a proximal phalanx. The base plate is ovoid shaped, having a substantially concave bearing surface 16 that is intended to contact and articulate with the head of the first metatarsal in the great toe joint, and a flat rear surface 28 opposite the concave bearing surface. A stem 18 projects from the rear surface 28 of the base plate away from the concave bearing surface 16 at an angle. The stem 18 is anatomically shaped to an intramedulary canal of a proximal phalanx. As illustrated in the top plan view of the stem in FIG. 2, the stem 18 has a general triangular gibbous shape 22, with the extent of the angular gibbosity decreasing as the stem is further away from the base plate 14 whereby the bottom 18 of the stem is almost shaped in a circle. In the preferred embodiments illustrated in FIGS. 5 to 12, the triangularity is more pronounced.

Figure 2:
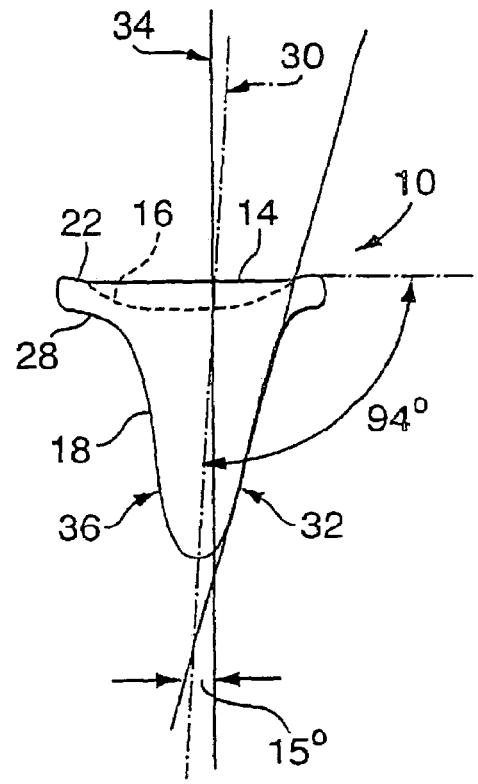
FIG. 2 is a side elevational view of the implant.

FIG. 2 is the side elevational view of implant 10 in accordance with the preferred embodiment, which shows a substantially symmetrical base 14 plate and stem 18 asymmetrical about the longitudinal axis 34 extending therefrom. The stem has a side 32 inclined with respect to the longitudinal axis 34 by about 15°. The centre 30 of the stem is angularly inclined by about 4° relative to the longitudinal axis 34 (about 94° relative to the base plate), following the angular relationship of the shaft to the proximal base of the proximal phalanx. The bearing surface 16 of the base plate has a rounded edge 22 around its periphery.

Figure 3:
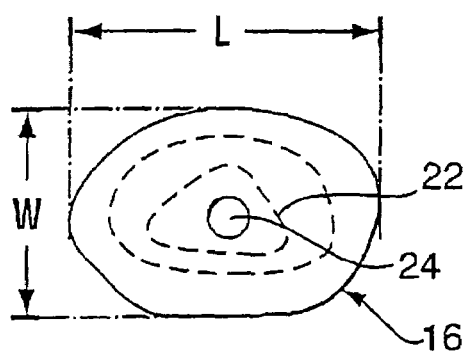
FIG. 3 is a top plane view of the implant.

The concave bearing surface 16 has a first radius of curvature along the vertical minor axis 32 and a second radius of curvature along the horizontal major axis 30. The appropriate lengths of radii of curvature for the first and second radii respectively for different sizes of implants are as follows: Small—about 0.504 in and about 0.325 in; Medium—about 0.535 in and about 0.374 in; Large—about 0.567 in and about 0.433 in. The corresponding lengths (L) and widths (W) (see FIG. 3) of the small, medium and large base plates are 0.65 in and 0.512 in; 0.728 in and 0.556 in; and 0.827 in and 0.63 in. The length of the stem must be sufficient to allow the implant to be anchored in to the proximal phalanx. The lengths of the stem of the implant for different sizes of implant are as follows: Small—about 0.485 in; Medium—about 0.563 in; Large—about 0.645 in. The thickness of the base plates for different sizes of implants are as follows: Small—about 0.079 in; Medium—about 0.079 in; Large—about 0.098 in. The two sides 32 and 36 of the stem projects form an angle about 22° at the top portio of the gibbosity and form an angle about 31° at the base portion of the gibbosity.

Figure 4:
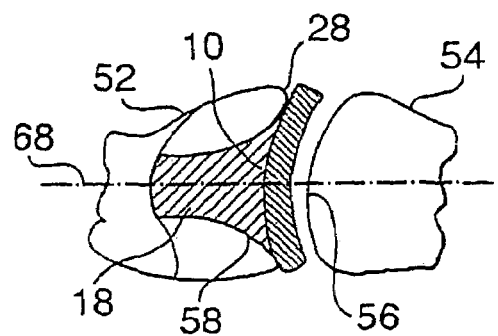
FIG. 4 is a partial cut-away skeletal representation of a side view of the implant in accordance when surgically implanted in the proximal phalanx.
Figure 5:
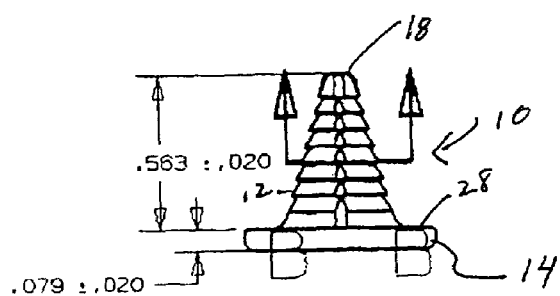
FIG. 5 is a side view of a proximal phalanx implant with fixator grooves.
Figure 6:
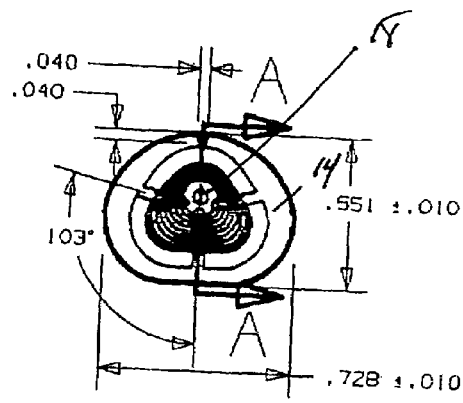
FIG. 6 is a top view of the implant of FIG. 5.
Figure 7:
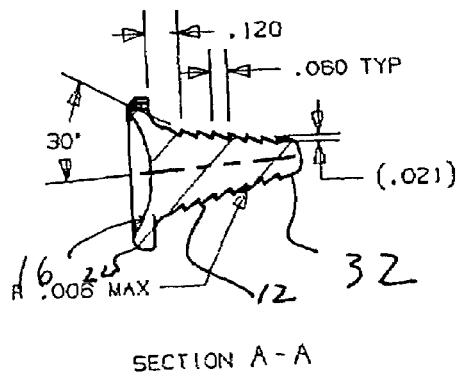
FIG. 7 is a section through line A—A in FIG. 6.

Referring to FIGS. 4, a great toe joint comprises a proximal phalanx 52 that has an implant 10 surgically implanted. Typically, a cut normal to the longitudinal axis 68 of the proximal phalanx at the proximal base is made to accommodate the implant which will replace the degenerated portion of a proximal phalanx. The rear surface 28 of the stem is placed against the resected proximal based of the phalanx 52 and an anatomically shaped stem 18 is implanted into the bone canal 58 of the proximal phalanx, and conforms to the cortex in the shaft.

Metatarsal bone 54 has a rounded head portion 56. In the preferred use of the implant 10, metatarsal head is the natural surface of metatarsal bone 54. However, it is equally within the scope of the invention to use implants on metatarsal bone 54 that provided a rounded artificial surface that articulates on implant 10.

The bearing surface 16 of the base plate 14 has a complex concave surface reciprocal to the anatomically convex head 56 of the metatarsal 54. Hence, the implant 10 provides a functional advantage by increasing surface contact between the bearing surface and consequently reducing localized loading between the implant 10 and the metatarsal 54.

The surface of the stem, as illustrated in FIGS. 5 to 8, is preferably ridged in parallel barb-like ridges 12, to permit the stem to be firmly anchored into an intramedular canal without the use of bone cement. Each ridge 12 comprises a flat portion facing the top of the implant, and an enclosed portion sloping toward the tip. Canals may be cut in the ridges, from top to bottom, to facilitate implantation, and to permit fluid to flow between ridges when the implant is in place.

It will be appreciated that the intramedulary canal will require less surface preparation using the surface-treated stem of the present invention, which will in fact grip to a fairly smooth surface even better than to a roughened surface. As the resected bone surface excites calcium fluids after the implant is in place, these will harden, and the bone will grow into the ridges in the stem.

Alternatively, the stem may be beaded, with a similar result and/or it may be coated with Hydroxy Appetite, to enhance adhesion to the resected bone surface.

Figure 8:
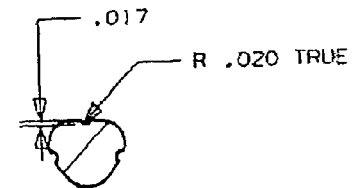
FIG. 8 is a section through line B—B in FIG. 5.
Figure 9:
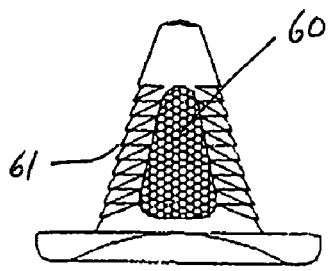
FIG. 9 is a front view of one preferred embodiment of the present invention.
Figure 10:
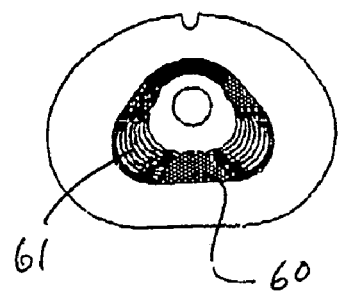
FIG. 10 is a top view of the embodiment shown in FIG. 9.

Referring to FIGS. 9 and 10, another preferred embodiment of the present invention is illustrated. The overall shape is as observed in FIGS. 5 to 8, but the surface treatment is significantly improved. As can be seen from the top view of FIG. 10, the stem of the implant is generally triangular in configuration, with fairly flat sides and curved corners. The applicant has determined that a strong grip between the implant and the intramedulary canal can be obtained by providing cross-hatching or checking 60 on the flat surfaces. The corners, however, are each provided with a stacked arrangement of arcuate ridges 61 that function much like barbs to grip the surface of the intramedulary canal when the stem is inserted therein.

Figure 11:
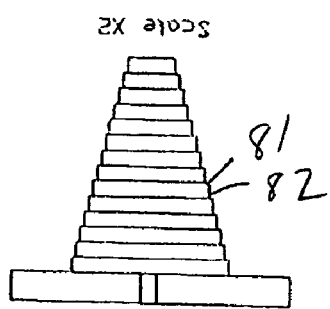
FIG. 11 is a front view of another preferred embodiment of the present invention.
Figure 12:
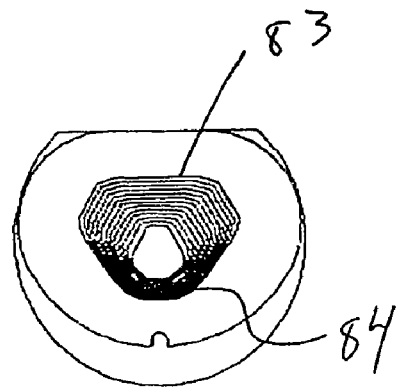
FIG. 12 is a top view of the embodiment shown in FIG. 11.

An alternative preferred embodiment is shown in FIGS. 11 and 12. In that embodiment, as shown in FIG. 8, a step-like configuration of ridges 81 and grooves 82 is provided on the surface of the stem, each step 81 and each groove 82 circumscribing the stem. The embodiment is particularly distinguished, however, in that its overall shape departs slightly from triangular or ovoid and is more pentagonal in conformation, with a fairly flat base 83 in opposition to an arcuate side 84.

The implant is preferably made from biocompatibility material Cobalt-28 chromium-6 molybdenum alloy. The bearing surface of the implant is highly polished to minimize wear.

Numerous modifications, variations and adaptations may be made to the particular embodiments of the invention described above without departing from the scope of the invention, which is defined in the claims. Moreover, it will be understood that the invention described herein is not limited to implants for MTP joints. The structures as described, modified appropriately, are suitable for use in resurfacing other joints as well.

The invention claimed is:

1. A prosthesis for implantation at the proximal articular surface of a proximal phalange, of a human great toe, comprising:
   a base portion having a generally concave bearing surface shaped to articulate with the distal articular surface of a metatarsal bone, and a flat surface opposite the bearing surface for emplacement against a resected surface of the proximal phalange of the great toe of the human subject; and
   a stem extending distally from said flat surface of said base portion, for implantation in the intramedulary canal of a proximal phalange of the great toe of the human subject, said stem having a generally frusto-conical shape, with a substantially oval wide end at the said flat surface of the base portion, tapering to a substantially circular end, said generally frustoconically shaped stem having a longitudinal axis that is inclined at an anatomical angle, of about 94° to the base portion, to align with the intramedulary canal of a proximal phalanx of the great of the human subject.

2. A prosthesis as claimed in claim 1, wherein said stem has a side surface that tapers inwardly.

3. A prosthesis as claimed in claim 2, wherein said side surface of said stem is somewhat flattened in three aspects, between the base and end of the stem.

4. A prosthesis as claimed in claim 1, wherein said surface of said stem is textured for adhesion to the inner surface of a said intramedulary canal.

5. A prosthesis as claimed in 1, wherein said surface of said stem is ridged in a series of ridges that extend around said stem, parallel to said base portion.

6. A prosthesis as claimed in claim 5, wherein said ridges are substantially barb-like.

7. A prosthesis as claimed in claim 6, wherein each said barb-like ridge includes a long flat portion almost parallel to the side surface of the stem, and a short inwardly directed portion at a greater angle to said side surface.

8. A prosthesis as claimed in claim 3, wherein said side surfaces of said stem, where flattened, are knurled by cross-hatching.

9. A prosthesis as claimed in claim 8, wherein said stem, in corner areas between said flattened aspects, is provided with barb-like ridges.

10. A prosthesis as claimed in claim 9, wherein each said barb-like ridge comprises an arcuate portion having a surface almost parallel to the side surface of said stem, and a short inwardly directed portion at a greater angle to said side surface.

* * * * *